US008919205B2

(12) United States Patent
Huang et al.

(10) Patent No.: US 8,919,205 B2
(45) Date of Patent: Dec. 30, 2014

(54) MEASURING DEVICE AND OPERATION METHOD THEREOF (71) Applicant: Industrial Technology Research Institute, Hsinchu (TW)

(72) Inventors: Guo-Shing Huang, Hsinchu County (TW); Cheng-Yi Shih, Hsinchu (TW); Chung-Huang Huang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 67 days.

(21) Appl. No.: 13/677,320

(22) Filed: Nov. 15, 2012

(65) Prior Publication Data

US 2014/0060201 A1    Mar. 6, 2014

(30) Foreign Application Priority Data

Sep. 6, 2012   (TW) .............................. 101132539 A (51) Int. Cl.
*G01N 3/08*     (2006.01)
(52) U.S. Cl.
CPC ....................................... *G01N 3/08* (2013.01)
USPC ............................................. 73/826; 73/159
(58) Field of Classification Search
CPC . G01N 3/08; G01N 2291/0237; G01B 21/20; G01B 7/087; G01F 1/692; B32B 17/10981
USPC .......................................... 73/159, 760, 826
See application file for complete search history.

(56) References Cited

U.S. PATENT DOCUMENTS

| | | | | |
|---|---|---|---|---|
| 3,264,878 A | * | 8/1966 | Balog | .......................... 73/865.8 |
| 3,592,091 A | * | 7/1971 | Ottavan | ........................... 83/879 |
| 3,839,959 A | * | 10/1974 | Abendroth | .................... 101/232 |
| 4,015,799 A | | 4/1977 | Koski et al. | |
| 4,580,132 A | * | 4/1986 | Kato et al. | ..................... 340/540 |
| 4,589,644 A | * | 5/1986 | Gratsch | ...................... 270/30.03 |
| 6,827,787 B2 | | 12/2004 | Yonezawa et al. | |
| 6,916,509 B2 | | 7/2005 | Yonezawa et al. | |
| 7,144,241 B2 | | 12/2006 | Hennessey et al. | |
| 7,510,901 B2 | | 3/2009 | Yonezawa et al. | |

(Continued)

FOREIGN PATENT DOCUMENTS

| | | |
|---|---|---|
| TW | 200844423 | 11/2008 |
| TW | 200911720 | 3/2009 |

(Continued)

OTHER PUBLICATIONS

Evan Schwartz, "Roll to Roll Processing for Flexible Electronics", Cornell University MSE 542, Flexible Electronics, May 2006, pp. 1-24.

(Continued)

*Primary Examiner* — Max Noori
(74) *Attorney, Agent, or Firm* — Jianq Chyun IP Office (57) ABSTRACT

A measuring device linked to a conveyor for transporting a flexible glass is provided. The measuring device includes a base, a first roller, and at least one second roller. The first roller disposed on the base moves back and forth along a first axis. The second roller disposed on the base moves back and forth along a second axis. The flexible glass enters the conveyor passing through the second roller and the first roller. An operation method of the measuring device is also provided.

15 Claims, 10 Drawing Sheets

(56) References Cited

U.S. PATENT DOCUMENTS

| | | |
|---|---|---|
| 7,522,053 B2 * | 4/2009 | Johnson et al. ............ 340/572.1 |
| 7,796,205 B2 | 9/2010 | Suzuki et al. |
| 7,883,778 B2 | 2/2011 | Nakamura et al. |
| 7,956,956 B2 | 6/2011 | Saitoh et al. |
| 7,968,353 B2 | 6/2011 | Britt et al. |
| 8,088,224 B2 | 1/2012 | Vasquez et al. |
| 8,114,248 B2 | 2/2012 | Lee et al. |
| 8,165,498 B2 * | 4/2012 | Hoshino et al. ............... 399/121 |
| 2006/0216618 A1 | 9/2006 | Horgan et al. |
| 2011/0192878 A1 | 8/2011 | Teranishi et al. |
| 2013/0134202 A1 * | 5/2013 | Garner et al. .................... 226/6 |

FOREIGN PATENT DOCUMENTS

| | | |
|---|---|---|
| TW | 201020183 | 6/2010 |
| TW | 201206849 | 2/2012 |
| TW | I358537 | 2/2012 |

OTHER PUBLICATIONS

Steffen Hoehla, et al., "Full Color AM-LCDs on Flexible Glass Substrates", ITE and SID, May 2011, pp. 1689-1692.

Kuan-Wei Wu, et al., "Color ChLC e-paper display with 100 um flexible glass substrates", SID, 29.3, May 2011, pp. 1-3.

Po-Yuan Lo, et al., "Flexible glass substrates for organic TFT active matrix electrophoretic displays", SID, 29.2, May 2011, pp. 1-2.

S. Garner, et al., "Flexible glass substrates for continuous manufacturing", FLEX, Feb. 2011, pp. 1-13.

"Office Action of Taiwan Counterpart Application", issued on Jul. 17, 2014, p. 1-p. 6.

* cited by examiner

MEASURING DEVICE AND OPERATION METHOD THEREOF

CROSS-REFERENCE TO RELATED APPLICATION

This application claims the priority benefit of Taiwan application serial no. 101132539, filed on Sep. 6, 2012. The entirety of the above-mentioned patent application is hereby incorporated by reference herein and made a part of this specification.

TECHNICAL FIELD

The disclosure is related to a measuring device and an operation method thereof.

BACKGROUND

Flexible glass has the characteristics of glass and flexible substrates. As the development of electronic products aims at being slimmer and lighter, the need to thinner glass increases due to the needs in elements such as planar substrates in e-Papers, and covers, touch-sensors, solid-state light-emitting elements, electronic devices, and photovoltaic modules.

As the thickness of glass decreases, the glass becomes more flexible. Therefore, the conventional flexible glass may be transported via roll-to-roll transportation. However, during manufacture of the flexible glass, it is still necessary to consider whether the flexible glass has qualified mechanical properties and endurance to impact. In addition, the flexible glass needs to be prevented from being damaged during transportation to ensure the yield rate of the flexible glass. The reason is that even though the glass is already flexible to a certain degree given that the glass is hardly flawed and extremely thin, the glass still maintains its material property of being brittle. Therefore, before the flexible glass is sent to undergo post-processes, it still needs to be tested to understand its material property of endurance, such as stress endurance.

SUMMARY

An embodiment of the disclosure provides a measuring device suited for linking to a conveyer and transporting a flexible glass. The measuring device includes a base, a first roller, and at least one second roller. The first roller is disposed on the base and moves back and forth along a first axis. The second roller is disposed on the base and moves back and forth along a second axis. The first axis is perpendicular to the second axis. The flexible glass enters the conveyor after passing through the second roller and the first roller.

An embodiment of the disclosure provides an operation method of a measuring device. The measuring device includes a base suitable to be linked to a conveyor in order for a flexible glass to pass through the base before entering the conveyor. The operation method of the measuring device includes: disposing a first roller on the base, wherein the first roller has a first external diameter; disposing at least one second roller on the base, wherein the second roller has a second external diameter; adjusting a position of the first roller on a first axis; adjusting a position of the second roller on a second axis; and driving the flexible glass to pass through the second roller and the first roller and then enter the conveyor.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
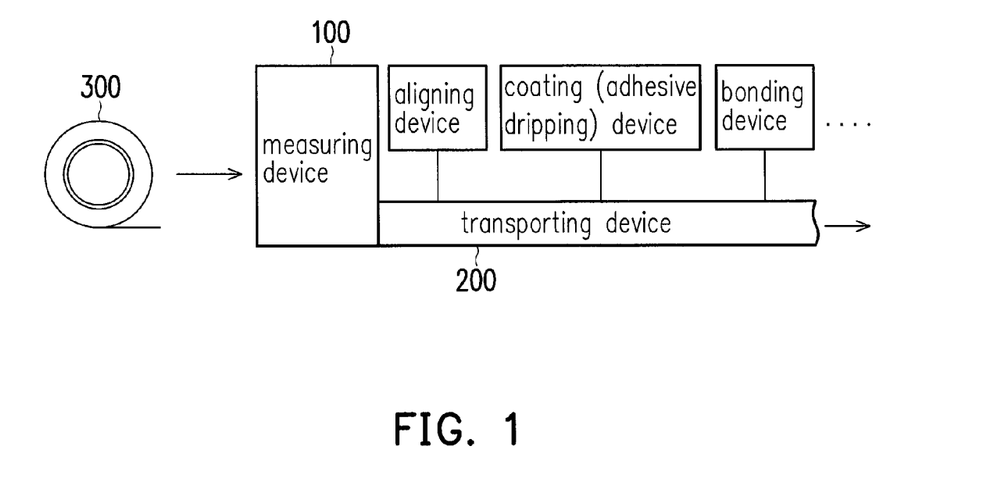
FIG. 1 is a processing flowchart of a flexible glass according to an embodiment of the disclosure.

FIG. 1 is a processing flowchart of a flexible glass according to an embodiment of the disclosure. Referring to FIG. 1, a glass has a flexible characteristic when a thickness of the glass is thin to a degree. Therefore, such glass is suitable to be transported by a roll-to-roll conveyor 200. During a transporting process, a flexible glass 300 may undergo a number of processes performed with a number of devices, such as an aligning device, a coating (adhesive dripping) device, and a bonding device, etc. illustrated in FIG. 1. However, the disclosure does not impose any limitation on types of processing devices disposed on the conveyor 200. However, to ensure that the flexible glass 300 has a qualified stress endurance during the transporting process, or to understand beforehand a material property of the flexible glass 300 for adjusting a processing condition or environment of a subsequent processing device, a measuring device 100 is required to further measure the flexible glass 300 before the flexible glass 300 of this embodiment enters the conveyor 200.

In addition, in other embodiments that are not shown here, the measuring device 100 may also be configured for a quality measurement after completion of manufacture of the flexible glass 300. Namely, the measuring device 100 may also be disposed at the end of a glass manufacturing device for related personnel to keep track of a yield rate of a manufacturing or processing device. For example, a processability of a batch of the flexible glass 300 is understood by making the flexible glass 300 pass different stress conditions of the measuring device to see if any defect (e.g. fracture) is found and obtain an endurance value of the flexible glass 300. In other words, the disclosure does not limit on a position at which the measuring device 100 is disposed.

The measuring device 100 of the disclosure may be additionally loaded to a device when a characteristic of the flexible glass 300 needs to be measured during the manufacturing or treating process of the flexible glass 300, such that the quality of the flexible glass 300 is ensured.

Figure 2:
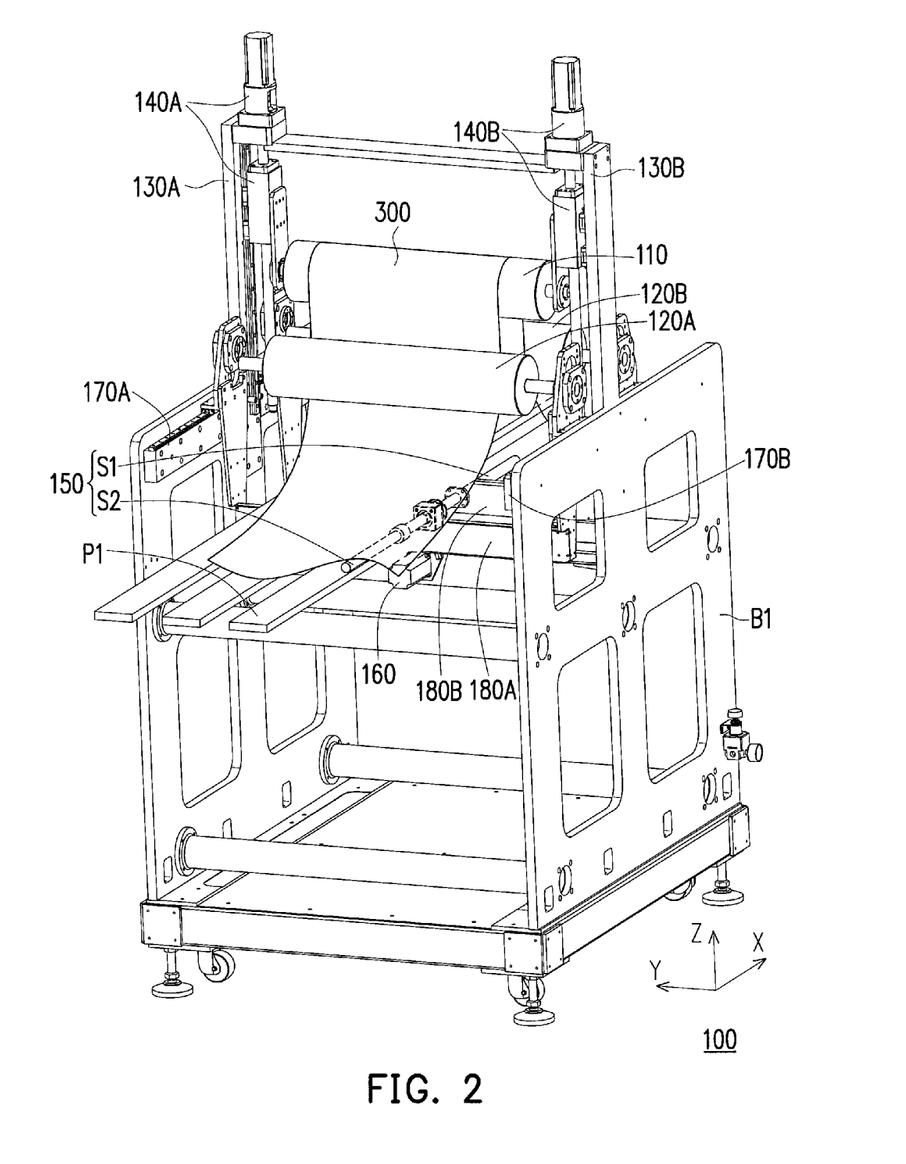
FIG. 2 is a schematic diagram of the measuring device of FIG. 1.

FIG. 2 is a schematic diagram of the measuring device of FIG. 1. A Cartesian coordinate is provided to clearly describe a relative position between elements. Referring FIGS. 1 and 2 simultaneously, in this embodiment, the measuring device 100 includes a base B1, a first roller 110, and a pair of second rollers 120A and 120B. The base B1 has a platform P1, which is located under the first roller 110 and the second rollers 120A and 120B and is engaged to the conveyor 200 to allow the flexible glass 300 to pass through the measuring device 100 via a moving path on which the flexible glass 300 proceeds via the platform P1 and rolls upon the first roller 110 and the second rollers 120A and 120B.

The first roller 110 and the second rollers 120A and 120B are respectively movably disposed on the base B1 to adjust a respective contact state of the flexible glass 300 with the first roller 110, the second roller 120A, and the second roller 120B, so as to further understand the stress endurance of the flexible glass 300 under different contact states.

More specifically, the measuring device 100 further includes a pair of first tracks 130A and 130B, and a pair of first moving components 140A and 140B, wherein the first tracks 130A and 130B are respectively disposed at two opposing sides of the base B1 along the Y-axis. Similarly, the first moving components 140A and 140B, such as a motor and a sliding block driven by the motor, are also disposed at the two opposing sides of the base B1 and slidably coupled onto the first tracks 130A and 130B. The first tracks 130A and 130B extend along the Z-axis, whereas the first moving components 140A and 140B also slide on the first tracks 130A and 130B along the Z-axis. Two opposing ends of the first roller 110 are connected between the pair of the first moving components 140A and 140B, and extend along the Y-axis. Thereby, the user may use a controller (not shown) to connect to the first moving components 140A and 140B and drive the first moving components 140A and 140B to slide on the first tracks 130A and 130B, so as to make the first roller 110 move back and forth along the Z-axis.

Moreover, the measuring device 100 further includes a screw rod 150, a second moving component 160, a pair of second tracks 170A and 170B, and a pair of moving frames 180A and 180B, wherein the second tracks 170A and 170B are respectively disposed on the two opposing sides of the base B1 along the Y-axis, and the moving frames 180A and 180B are coupled between the pair of the second tracks 170A and 170B. The second tracks 170A and 170B extend along the X-axis, and the second rollers 120A and 120B are respectively mounted on the moving frames 180A and 180B, and respectively extend along the Y-axis.

In addition, the screw rod 150 penetrates through the moving frames 180A and 180B along the X-axis and is screw-connected to the moving frames 180A and 180B. The second moving component 160, such as a motor and a bearing connected to the motor, is connected to and drives the screw rod 150 to rotate. Thereby, the user may drive the second moving component 160 with the controller, so as to drive the moving frames 180A and 180B as well as the second rollers 120A and 120B on the moving frames 180A and 180B to move back and forth along the X-axis.

FIGS. 3 to 6 are schematic diagrams illustrating the first roller and the second roller of FIG. 2 in a different state. Referring to FIGS. 2-6, it should be noted that the screw rod 150 of this embodiment has a first section S1 and a second section S2 having opposite screw threads, wherein the moving frame 180A is screw-connected to the first section S1, and the moving frame 180B is screw-connected to the second section S2. Thereby, the user is allowed to simultaneously drive the two moving frames 180A and 180B to move with merely the single second moving component 160, such that the moving frames 180A and 180B move toward or away from each other along the X-axis. In another embodiment not shown here, a screw rod with different driving devices or screw pitches may be configured to further change a moving distance of the second rollers.

Figure 5:
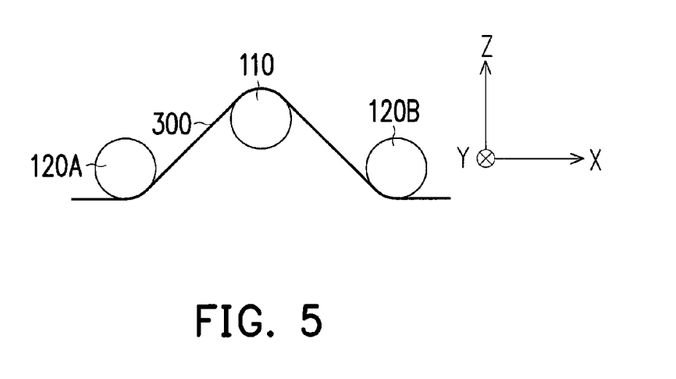
Figure 6:
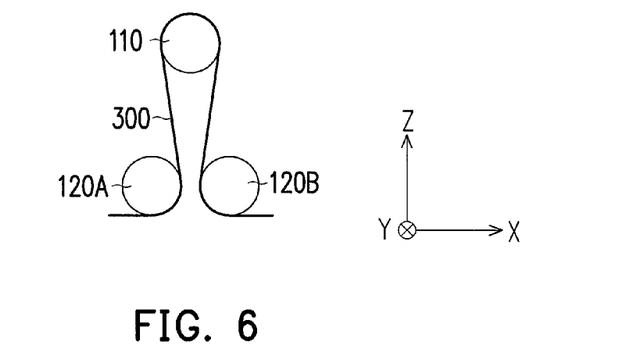
Figure 7:
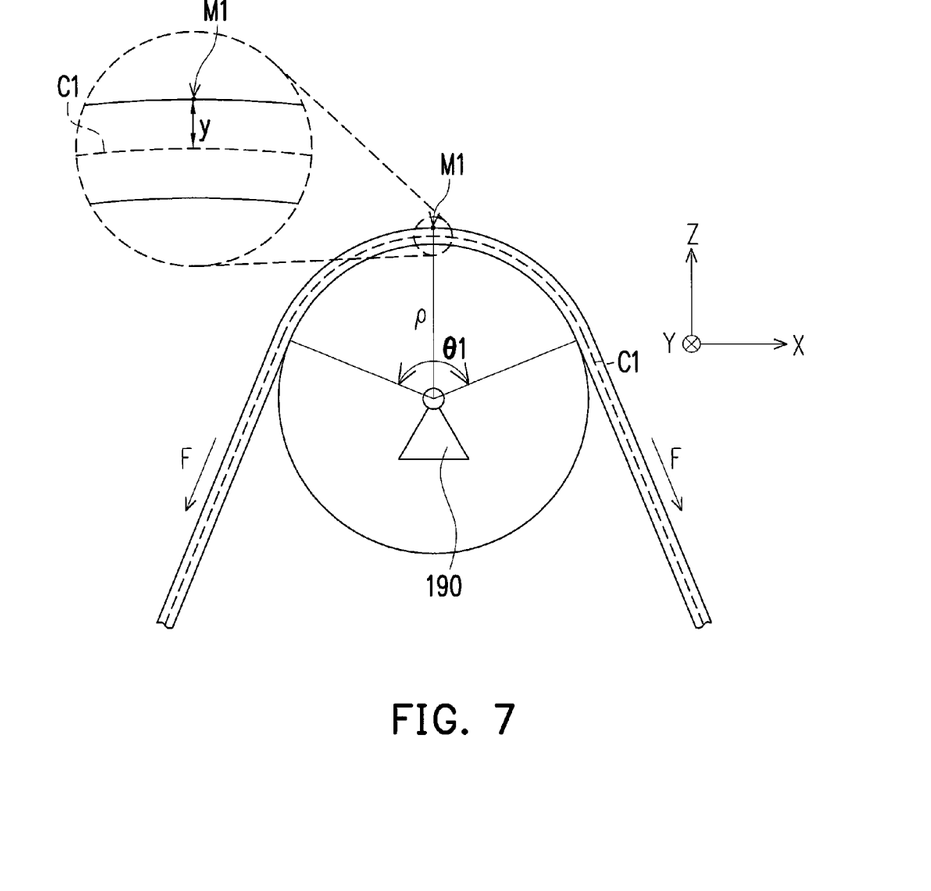
FIG. 7 is a schematic diagram of a part of the first roller of FIG. 5.

FIG. 7 is a schematic diagram of a part of the first roller of FIG. 5. Referring to FIG. 7, in this embodiment, the states illustrated in FIGS. 3 to 6 between the flexible glass 300 on the first roller 110 and the first roller 110 occur by adjusting relative positions of the first roller 110 and the second rollers 120A and 120B.

Thereby, the stress endurance of the flexible glass 300 is known. In terms of bending stress, the bending stress varies with a thickness direction of glass. Taking FIG. 7 for example, a bending stress $\sigma 1$ of the flexible glass 300 at a point M1 is:

$$\sigma 1 = (Ey)/\rho$$

In the formula, E stands for Young's modulus, y is a distance of the point M1 from a bending centerline C1, and $\rho$ is a bending radius.

Figure 3:
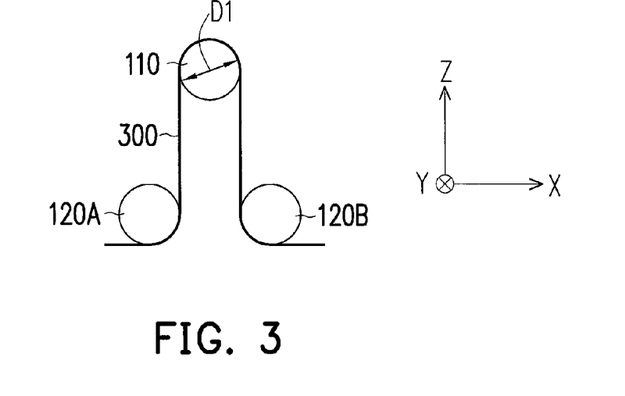
FIGS. 3 to 6 are schematic diagrams illustrating the first roller and the second roller of FIG. 2 in a different state.
Figure 4:
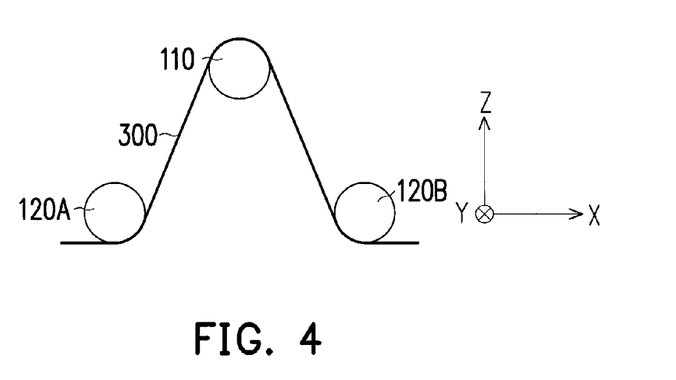
Figure 8:
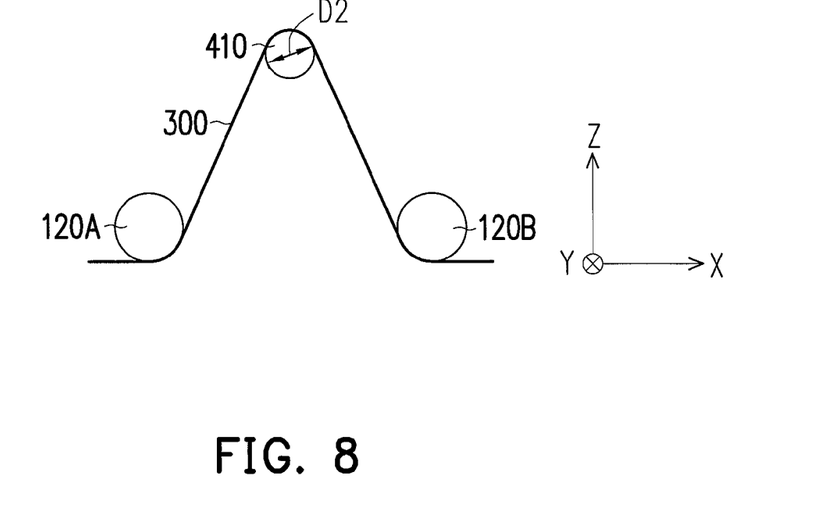
FIG. 8 is a schematic diagram of the flexible glass and roller according to an embodiment of the disclosure in another state.
Figure 8A:
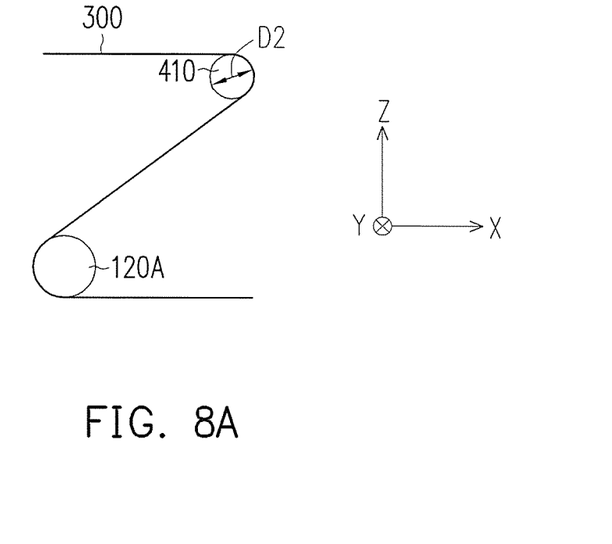

It can be known that a bending stress that the flexible glass 300 takes is only related to a roller radius. The larger the roller radius, the lower the bending stress the flexible glass takes. The smaller the roller radius, the higher the bending stress the flexible glass takes, the bending stress is stronger. FIG. 8 is a schematic diagram of the flexible glass and roller according to an embodiment of the disclosure in another state. Referring to FIG. 8 and comparing FIG. 8 to FIG. 3, the first roller 110 has a diameter D1 in the embodiment of FIG. 3, whereas a first roller 410 has a diameter D2 in the embodiment of FIG. 8, wherein D1 is larger than D2. Therefore, a bending stress taken by the flexible glass 300 in FIG. 3 is smaller than a bending stress taken by the flexible glass 300 in the state illustrated in FIG. 8. On such basis, the user understands an endurance of the flexible 300 to the bending stress by changing rollers with different diameters. It should be noted that although the embodiments in FIGS. 3 and 8 use the first roller 110 or 410 as a subject matter of description, the disclosure is not limited thereto. In another embodiment not shown here, a measuring means described above may be applied with the second roller (e.g. the second roller 120A or 120B illustrated in FIG. 3). In other words, any roller on the measuring device may be adjusted with a measuring means similar to the one described above in order to observe a rolling state between the roller and the flexible glass when the flexible glass passes through the roller to understand the endurance of the flexible glass to different bending stresses. For example, in another embodiment that is not shown here, an effect identical to the embodiments above is also achieved by using only one first roller and one second roller and making the flexible glass roll thereupon and move in a Z-shaped path.

In addition, referring to FIG. 7, a wrap angle $\theta 1$ between the flexible glass 300 and the first roller 110 influences a range of the bending stress in the flexible glass 300. When the wrap angle $\theta 1$ is smaller, the range of the bending stress in the flexible glass 300 becomes smaller. When the wrap angle $\theta 1$ is larger, the range of the bending stress in the flexible glass 300 becomes larger. Therefore, the user is allowed to adjust the relative positions of the first roller 110 and the second rollers 120A and 120B, as illustrated in FIGS. 3-6, to adjust a size of the wrap angle $\theta 1$. Similarly, a measurement of the wrap angle $\theta 1$ is not limited to the flexible glass 300 and the first roller 110. The same means may also be applied between the flexible glass 300 and the second rollers 120A or 120B.

Moreover, the measuring device 100 further includes a load sensor 190 disposed on the first roller 110. The load sensor 190 is configured to measure a load applied on the first roller 110 along the Z-axis when the flexible glass 300 passes through the first roller 110. In other words, a tensile stress σ2 of the flexible glass 300 may be measured with the load sensor 190, as shown in the following:

$$\sigma2=F/(wt)$$

In the formula, F stands for tensile force, w is a width of the flexible glass 300 (i.e. a size of the Y-axis), and t is a thickness of the flexible glass 300.

With the above-described means, the user knows that a compound stress of the flexible glass 300 in one of the states is (σ1+σ2), and understands different degrees of endurance of the flexible glass 300 under different stress conditions, thereby understanding a processability of the flexible glass 300.

Figure 9:
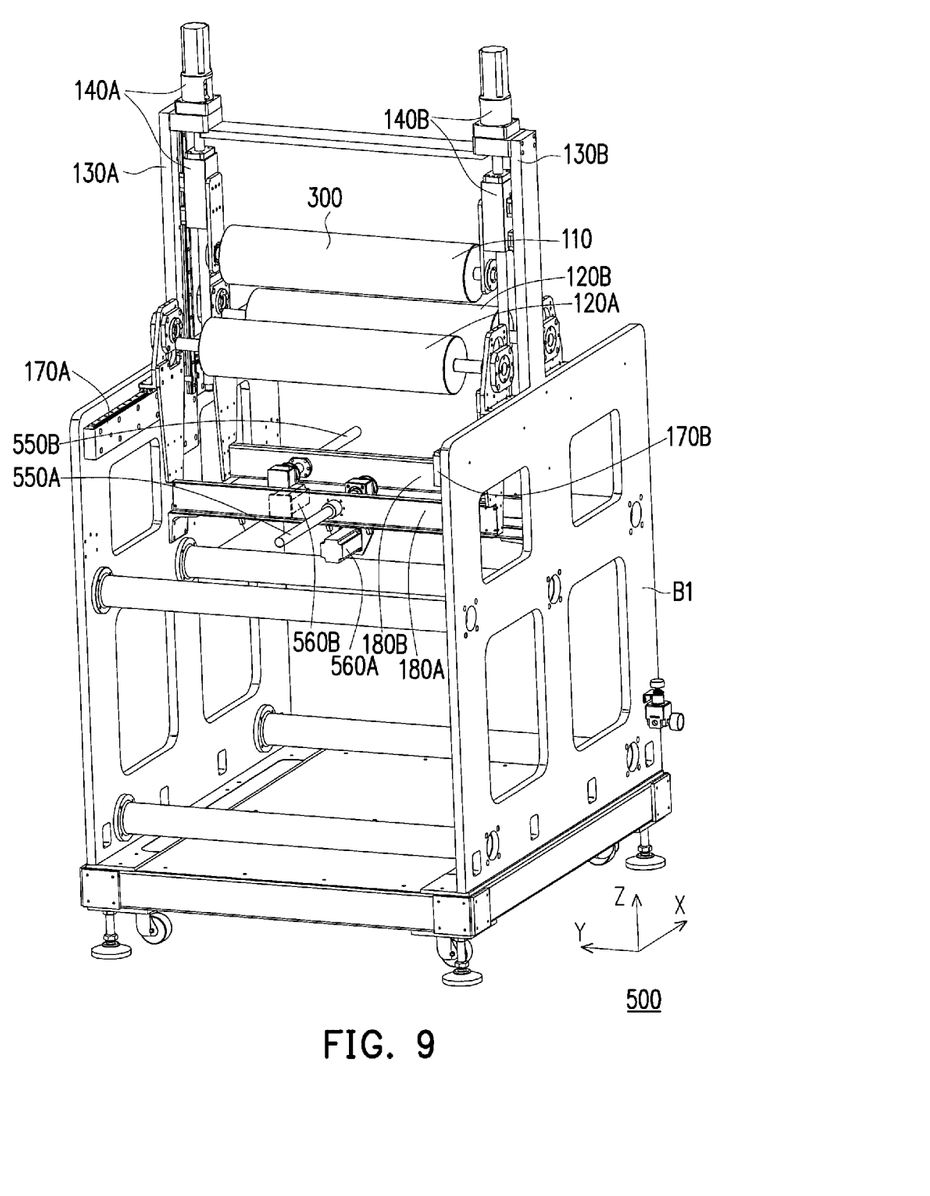
FIG. 9 is a schematic view of a measuring device according to another embodiment of the disclosure.
Figure 10:
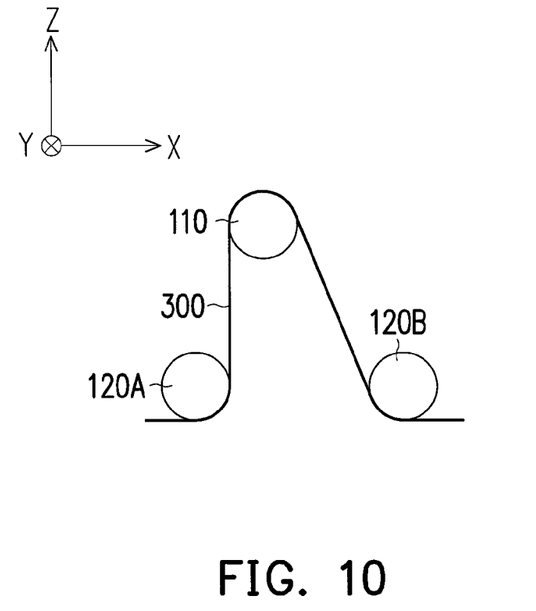
FIGS. 10 to 13 illustrate measuring states that occur in the measuring device of FIG. 9.
Figure 11:
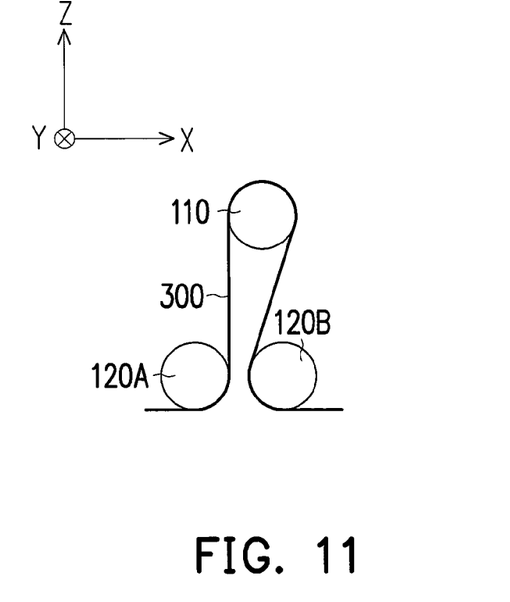
Figure 12:
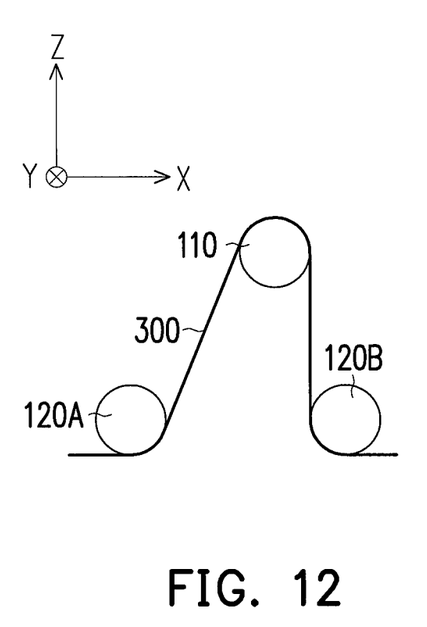
Figure 13:
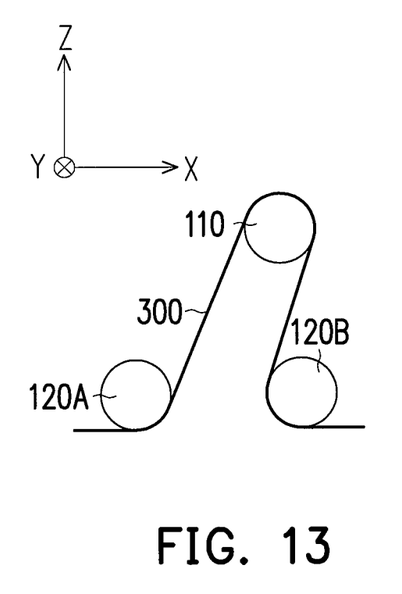

FIG. 9 is a schematic view of a measuring device according to another embodiment of the disclosure. Some elements are omitted here to clearly identify characteristics of a screw rod and second moving component. FIGS. 10 to 13 illustrate measuring states that occur in the measuring device of FIG. 9. Referring to FIG. 9 and comparing FIG. 9 to FIG. 2, what differs from the above-mentioned embodiment is that a measuring device 500 includes a pair of screw rods 550A and 550B and a pair of second moving components 560A and 560B, wherein the screw rods 550A and 550B penetrate through the moving frames 180A and 180B along the X-axis and are screw-connected to the moving frames 180A and 180B, and the second moving components 560A and 560B are respectively connected to and drive the screw rods 550A and 550B to rotate. Thereby, the user is allowed to respectively drive the moving frames 180A and 180B as well as the second rollers 120A and 120B on the moving frames 180A and 180B to move back and forth along the X-axis, so as to achieve the different states illustrated in FIGS. 10-13.

Figure 14:
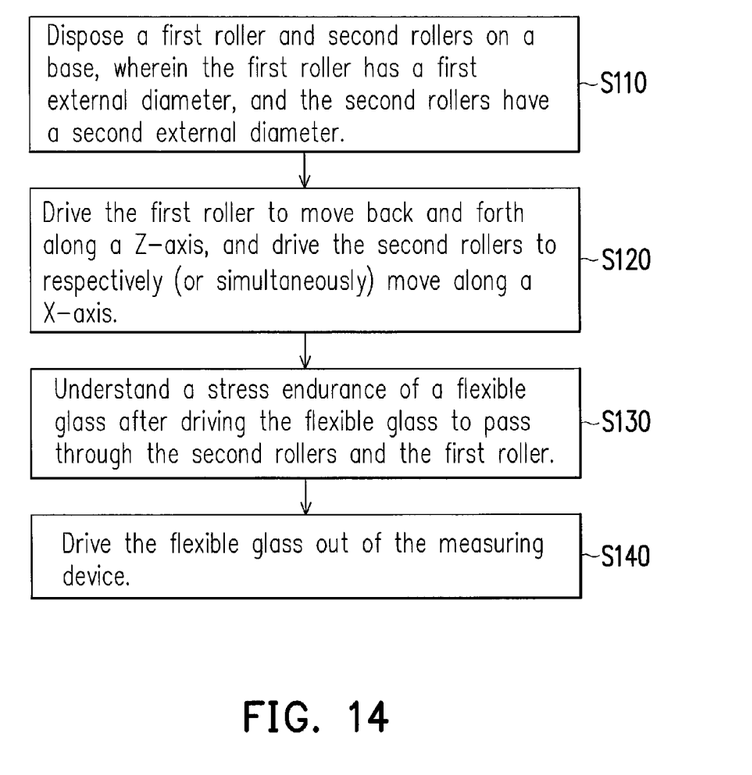
FIG. 14 illustrates a measuring flowchart according to the measuring device of the disclosure.

FIG. 14 illustrates a measuring flowchart according to the measuring device of the disclosure. Referring to FIG. 14 and the measuring device in the embodiments described above. At step S110, the first roller 110 and the second rollers 120A and 120B are disposed on the base B1, wherein the first roller 110 has a first external diameter, and each of the second rollers 120A and 120B has a second external diameter. It can be known from the embodiments that the first and second diameters may be identical to or different from each other, depending on the rollers with identical or different diameters as the basis of measurement based on the material property of the flexible glass 300 and subsequent processing conditions. Similarly, at step S120, the user may drive the first roller 110 to move back and forth along the Z-axis, and drive the second rollers 120A and 120B to respectively (or simultaneously) move along the X-axis, so as to determine the wrap angle θ1 (shown in FIG. 7) between the flexible glass 300 and the rollers 110, 120A, or 120B. At step 130, the stress endurance of the flexible glass 300 is determined by observing whether a defect is found on the flexible glass 300 after the flexible glass 300 is driven to pass through the second roller 120A, the first roller 110, and the second roller 120B. At the last step, step S140, the flexible glass 300 is driven out of the measuring device 100. At this time, the measuring device 100 may also be engaged prior to the conveyor 200 (as shown in FIG. 1), to allow various processing devices to perform subsequent processes to the flexible glass 300.

In view of the above, in the embodiments of the disclosure, the stress endurance of the flexible glass is known with the measuring device, wherein a size of the diameter and configuration of relative positions of the rollers may be modified by the user according to the material property and subsequent processing condition. Thereby, the measuring device is allowed to measure the flexible glass with different stress conditions. Moreover, by engaging the measuring device to another manufacturing or processing device, the measuring device is allowed to function as a measuring station after the flexible glass is manufactured or before the flexible glass is processed, so as to ensure the product quality of the flexible glass and improve the manufacturing yield rate of the subsequent process.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A measuring device, linking with a conveyor for transporting a flexible glass, comprising:
   a base;
   a first roller, disposed on the base and being adjustable along a first axis;
   at least one second roller, disposed on the base and being adjustable along a second axis, wherein the flexible glass enters the conveyor after passing through the second roller and the first roller; and
   a load sensor, disposed on the first roller and configured to measure a tensile force applied along the first axis by the flexible glass while passing through the first roller.

2. The measuring device as claimed in claim 1, further comprising:
   a pair of first tracks, disposed on the base oppositely and parallel to the first axis; and
   a pair of first moving components, respectively disposed on the pair of first tracks, wherein the first roller is connected between the pair of first moving components, to the first roller moves back and forth with the pair of first moving components on the pair of first tracks along the first axis.

3. The measuring device as claimed in claim 1, further comprising a pair of second rollers, wherein on a transporting path of the flexible glass, the first roller is located between the pair of second rollers, and the pair of second rollers move toward or away from each other along the second axis.

4. The measuring device as claimed in claim 3, further comprising:
   a pair of second tracks, disposed at two opposite sides of the base and parallel to the second axis; and
   a pair of moving frames, wherein each of the pair of moving frames is coupled between the pair of second tracks, and the pair of second rollers are respectively disposed on the pair of moving frames, to the pair of second rollers move back and forth with the moving frames along the second axis.

5. The measuring device as claimed in claim 4, further comprising:
   a screw rod, penetrating through the pair of moving frames along the second axis and screw-connected to the pair of moving frames; and
   a second moving component, connected to and driving the screw rod, wherein the pair of moving frames and the pair of second rollers thereon are moved back and forth by the second moving component along the second axis.

6. The measuring device as claimed in claim 5, wherein the screw rod has a first and a second sections having opposite screw threads, one of the moving frames is screw-connected to the first section, and the other of the moving frames is screw-connected to the second section.

7. The measuring device as claimed in claim 4, further comprising:
   a pair of screw rods, respectively penetrating through the pair of moving frames along the second axis and screw-connected to the pair of moving frames; and
   a pair of second moving components, respectively connected to and driving the pair of screw rods, wherein the pair of moving frames and the pair of the second rollers thereon are moved back and forth by the pair of second moving components along the second axis.

8. The measuring device as claimed in claim 3, wherein the pair of second rollers are located on an identical horizontal plane.

9. The measuring device as claimed in claim 1, wherein the first axis is perpendicular to the second axis.

10. The measuring device as claimed in claim 1, wherein the first roller has a first external diameter, the second roller has a second external diameter, and the first external diameter is equivalent to the second external diameter.

11. The measuring device as claimed in claim 1, wherein the first roller has a first external diameter, the second roller has a second external diameter, and the first external diameter is not equivalent to the second external diameter.

12. The measuring device as claimed in claim 3, wherein the pair of second rollers have different external diameters.

13. The measuring device as claimed in claim 1, wherein the first roller has a first external diameter, and the first external diameter is changeable.

14. The measuring device as claimed in claim 1, wherein the second roller has a second external diameter and the second external diameter is changeable.

15. The measuring device as claimed in claim 1, wherein an bending stress of the flexible glass is specified by changing the first or/and the second rollers with different diameters.

* * * * *